United States Patent [19]
Bosslet et al.

[11] Patent Number: 5,643,731
[45] Date of Patent: Jul. 1, 1997

[54] USE OF PAIRS OF LEUCINE ZIPPER PEPTIDES IN IMMUNOASSAY METHODS

[75] Inventors: Klaus Bosslet; Peter Hermentin; Hans Harald Sedlacek; Bernhard Auerbach; Peter Pfleiderer; Rolf Müller, all of Marburg, Germany

[73] Assignee: Behringwerke Aktiengesellschaft, Marburg, Germany

[21] Appl. No.: 467,943

[22] Filed: Jun. 6, 1995

Related U.S. Application Data

[63] Continuation of Ser. No. 342,001, Nov. 16, 1994, abandoned, which is a continuation of Ser. No. 182,390, Jan. 18, 1994, abandoned, which is a continuation of Ser. No. 27,587, Mar. 5, 1993, abandoned, which is a continuation of Ser. No. 805,687, Dec. 12, 1991, abandoned.

[30] Foreign Application Priority Data

Dec. 19, 1990 [DE] Germany ............ 40 40 669.5

[51] Int. Cl.⁶ ............................................. G01N 33/53
[52] U.S. Cl. ................ 435/7.1; 435/7.5; 435/7.9; 435/7.92; 435/969; 435/971; 435/975; 436/518; 436/538; 436/824
[58] Field of Search .................... 435/7.1, 75, 7.9, 435/7.92, 7.93, 7.94, 7.95, 969, 971, 975; 436/518, 538, 824

[56] References Cited

U.S. PATENT DOCUMENTS 4,228,237 10/1980 Hevey et al. .................... 435/5

FOREIGN PATENT DOCUMENTS 0 177 191 4/1986 European Pat. Off. .
2 084 431 4/1982 United Kingdom .

OTHER PUBLICATIONS

P. Tijssen, Elsevier, Practice And Theory of Enzyme Immunoassays, 297–328 (1988).
M. Wilchek & E.A. Bayer, Applications of Avidin–Biotin Technology: Literature Survey, Methods in Enzymology, vol. 184, 14–15 (1990).
G. Paganelli et al., Radiolocalisation of Tumor Pretargeted by Biotinylated Monoclonal Antibody Advances in the Applications of Monoclonal Antibodies in Clinical Oncology; abstracts (1990).
E.K. O'Shea et al., Preferential Heterodimer Formation by Isolated Leucine Zippers from Fos and Jun, Science, vol. 245, 646–648 (1989).
M. Neuberg et al., A Fos Protein Containing the Jun Leucine Zipper Forms a Homodimer Which Binds to the AP1 Binding Site, Science, vol. 341, 243–245 (1989).
Koehler et al., Continuous Cultures of Fused Cells Secreting Antibody of Predefined Specificity, Nature, vol. 256, pp. 495–497 (1975).

(List continued on next page.)

*Primary Examiner*—Lora M. Green
*Attorney, Agent, or Firm*—Finnegan, Henderson, Farabow, Garrett & Dunner, L.L.P.

[57] ABSTRACT

The invention relates to a method of using a pair of leucine zipper peptides for in vitro diagnosis, in particular, for the immunochemical detection and determination of an analyte in a biological liquid. In one method, the first leucine zipper peptide is immobilized by attaching it to a solid support, the second leucine zipper peptide is coupled to a specific binding partner for the analyte, the two peptides are brought into contact, the sample of the biological liquid is brought into contact with the immobilized first peptide and the specific binding partner for the analyte, and the amount of analyte bound to the binding partner is determined. The leucine zipper peptides are preferably v-fos and c-jun.

14 Claims, 4 Drawing Sheets

OTHER PUBLICATIONS

Staehl et al., High Frequencies of Antigen–Specific Hybridomas: Dependence on Immunization Parameters and Prediction by Spleen Cell Analysis, J. Immunol. Meth. 32, 297–304 (1980).

Tanamori et al., A Sandwich Enzyme Immunoassay of Rabbit Immunoglobulin G With a New Solid Support, J. Immunol. Meth. 62, 123–131 (1983).

Strasburger et al., J. Biol. Chem; vol. 4, 112–118 (1989).

Adamkiewicz, et al., Oncogene 5(4), 524–535 (1990).

I SOLID - PHASE

BY ADSORPTION

BY COVALENT BOND

COVALENTLY BOUND TO ADSORBED CARRIER

COVALENTLY BOUND TO ADSORBED CARRIER

ZIPPER PROTEIN/PEPTIDE [e.g. JUN AND FOS]

SPECIFIC BINDING PARTNER IN THE ASSAY [e.g. ANTIBODY, LECTIN, ANTIGEN RECEPTOR ETC.]

SOLID - PHASE [e.g. MAGNETIC PARTICLE, LATEX, POLYSTYROL TUBES, SHEET - LIKE SOLID - PHASES ETC.]

CARRIER MOLECULE [e.g. PROTEIN]

II CONJUGATE

III AMPLIFICATION SYSTEM

FIG. 3B  COUPLING COMPOUND
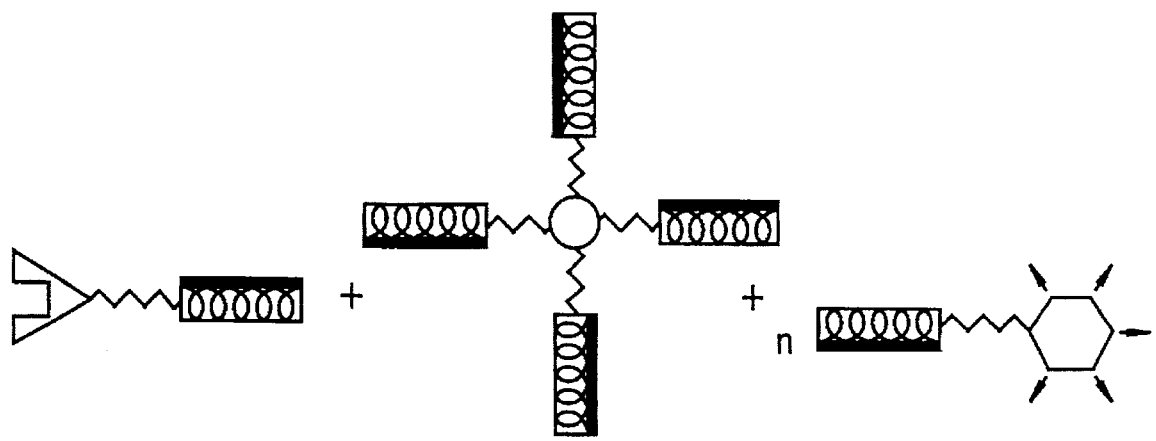
FIG. 3C  PREFORMED COMPLEX
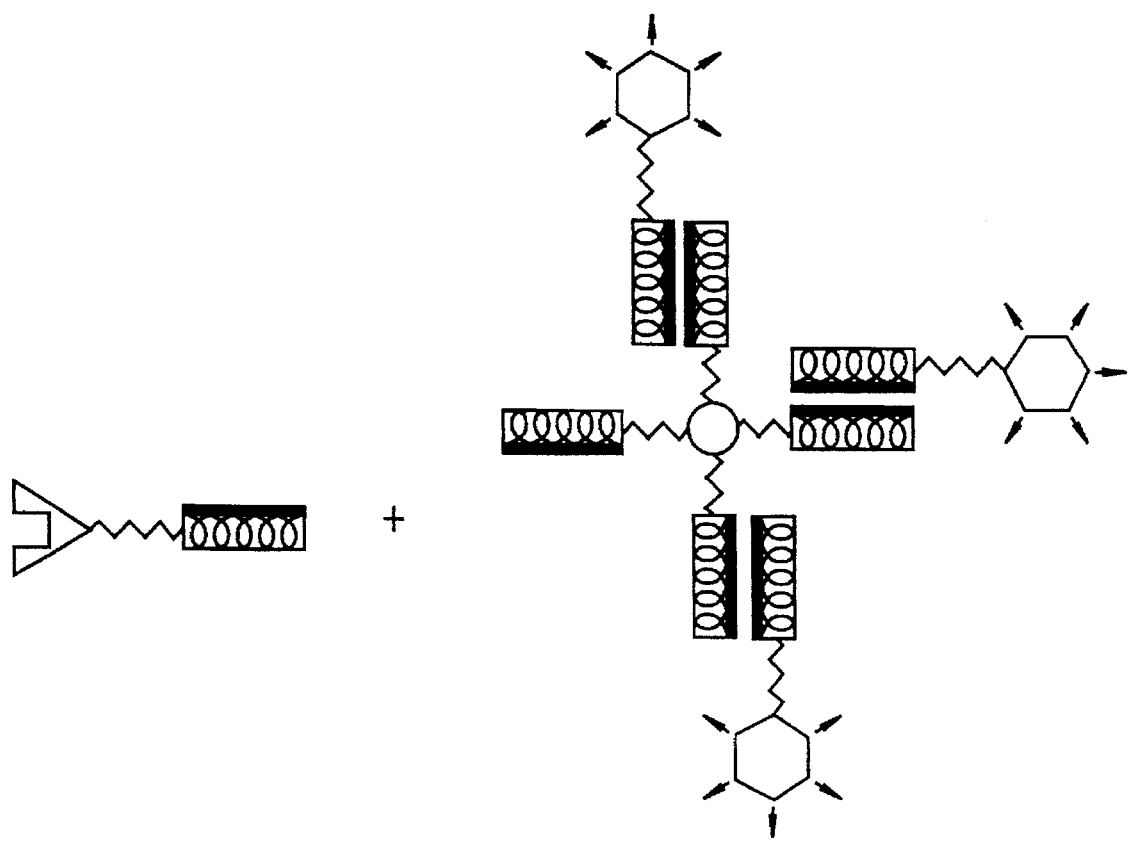

IV ARTIFICIAL CONTROLS/STANDARDS

ANTIGEN [e.g. PEPTIDE, PROTEIN, RECEPTOR, ENZYME, ANTIBODY, ANTIBODY FRAGMENT]

BINDING PARTNER SPECIFIC FOR AN ANTIGEN

USE OF PAIRS OF LEUCINE ZIPPER PEPTIDES IN IMMUNOASSAY METHODS

This is a continuation of Ser. No. 08/342,001, filed Nov. 16, 1994, now abandoned, which is a continuation of Ser. No. 08/182,390, filed Jan. 18, 1994, now abandoned, which is a continuation of Ser. No. 08/027,587, filed Mar. 5, 1993, now abandoned, which is a continuation of Ser. No. 07/805,687, filed Dec. 12, 1991, now abandoned.

The invention relates to the use of certain peptides with extremely high affinity for other peptides (heterodimer formation) and low affinity for themselves (homodimer formation) in the area of in vitro diagnosis.

Numerous examples in which two (bio)molecules are able to display high binding affinities for one another owing to highly favored interactions are known. An example which may be referred to here is the specific, directed interactions between antibodies and antigens on the basis of which immunological processes take place and whose practical use has greatly enriched in vitro diagnosis. The use of such specific binding partners (for example monoclonal antibodies, lectins, receptors etc.) has made it possible to recognize highly specific antigens of diagnostic relevance. Besides the question of specificity, that of the sensitivity is of equal importance for the detection of biocomplexes for diagnosis.

It has proven expedient, for various reasons, in diagnostic methods in which a specific binding partner of an analyte attached, for example covalently or by adsorption, to a solid phase, that this specific binding partner be coupled to the solid phase (hereinafter called "universal solid phase") not directly but via another specific binding pair which does not react with the analyte.

It has furthermore proven expedient in methods in which the use of the specific biomolecules is limited by their stability and potency that it may be sensible to use, even in the case of certain reagents, for example enzyme conjugates, a corresponding indirect method, i.e. that the specific binding partner is linked to the signal-emitting component via another specific binding pair which does not react with the analyte or the first specific binding partner.

This makes it possible, for example, to employ a "universal conjugate" for various analytes.

To achieve a "universal solid phase", for example mouse immunoglobulin-specific reagents such as anti-mouse antibodies or antibody-specific reagents such as protein A are used and are applied to the solid phase by conventional methods (Practice and Theory of Enzyme Immunoassays, P. Tijssen, Elsevier, 1988). The attractiveness of this idea is based on, inter alia, the fact that a solid phase prepared in this way is able to bind each specific mouse antibody in a directed manner and reproducibly because of immunological reaction. The use of a solid phase prepared in this way is possible in principle as classical stationary solid phase ("ready-to-use reagent") or else in homogeneous phase during the immunological reaction.

Immunochemical detection methods and specifically heterogeneous immunochemical detection methods are known per se to the person skilled in the art. Disadvantages of the known "universal solid phases" which may be mentioned here are the limitation exclusively to antibody coatings, as well as the limitation to certain assay setups (no completely monoclonal ELISA versions, no antigen solid phases).

It is furthermore known that samples with appreciable HAMA titers (HAMA=human anti-mouse antibodies) may after in vivo administration of monoclonal antibodies to humans cause very sensitive interference with such assay designs, and especially those carried out in homogeneous phase, and thus false diagnostic conclusions may be drawn.

Another system for putting said ideas into practice is that with biotin/avidin (for example U.S. Pat. No. 4,228,237). There is no doubt that it occupies a special position with regard to the high resulting binding strengths which can be observed. The wide range of uses of this system is described in a review article (Methods in Enzymology, Vol. 184 (1990), Avidin-Biotin Technology, Ed. Meir Wilchek; E. A. Bayer).

However, the disadvantages of the avidin molecule originate from the nature of this component of the system in in vitro diagnosis. Thus, the glycoprotein avidin has an exceptionally high isoelectric point (pI) and therefore at a neutral pH, that is to say under physiological conditions, displays, as a molecule with a strongly positive charge, strong non-specific interactions with negatively charged molecules such as, for example, nucleic acids, phospholipids, etc., as well as with charged surfaces. It is furthermore known that it is not possible to prepare defined and strictly reproducible products because of the microheterogeneities of the glycoproteins. Furthermore, the carbohydrate portion in the molecule contributes to unwanted side reactions with other biological molecules (for example "endogenous lectin") which may lead to distinct losses of sensitivity. The literature citation which has already been mentioned contains a note about the unwanted binding of avidin to endogenous lectin.

These disadvantages can be largely avoided by using the analog streptavidin from the bacterium Streptomyces avidinii. The latter has almost the same levels of affinity for biotin. It has a pI around the neutral point and, furthermore, does not have any carbohydrates in the molecule either. Nevertheless, fundamental problems arise with the streptavidin/biotin system too and may result in sensitive interference and, when used in in vitro diagnosis, possibly in unreliable results. It is known that the vitamin biotin is required by all living cells and is thus ubiquitous in all tissues and body fluids. Thus, for example, the concentration of biotin in human serum is approximately 10 ng/ml. This results in there being, in all diagnostic applications, a competition of the reagent with the sample material whose biotin content may vary to different extents depending on the physiological condition of the individual and his dietary habits (for example intake of multivitamin products).

Another serious potential interference results from the in vivo use of the streptavidin/biotin system (G. Paganelli et al., Radiolocalisation of tumour pretargeted by biotinylated monoclonal antibody; Advances in the applications of monoclonal antibodies in clinical oncology; abstracts). The procedure for this is to administer a biotinylated antibody, followed about 3–5 days later by indium-labeled streptavidin. It is known that both avidin and streptavidin are highly immunogenic substances and therefore result in a response in humans after administration. Reference is made in this context to so-called HASAs, that is to say human anti-streptavidin antibodies, which may lead to serious problems in assay designs in serum diagnosis.

The object of the present invention was to provide a high-affinity system for use in in vitro diagnosis, which does not have the abovementioned disadvantages. Moreover, the intention was that the individual components be obtainable easily, reproducibly and contamination-free with established procedures.

The method according to the invention is based on the exceptionally strong interactions of peptide segments of certain proteins which are able to bind DNA and thus are capable of modulating transcription. It has been found that the binding of, for example, the fos gene product to the jun gene product takes place with the formation of a heterodimer of exceptional strength. This binding furthermore shows resistance to high concentrations of chaotropic substances (for example urea), detergents and salt and to low and very high pH values. Comparable heterodimer binding strengths have been measured with synthetic peptides which comprise amino-acid positions 285 to 324, the so-called leucine zipper of the c-Jun protein (SEQ ID No1), and positions 162 to 201, the leucine zipper of the v-Fos protein (SEQ ID No2). These peptides have the following amino-acid sequence:

c-Jun "leucine zipper peptide" (SEQ ID No:1):
RIARLEEKVKTLKAQNSELASTANMLREQVAQ LKQKVMNY v-Fos "leucine zipper peptide" (SEQ ID No2):
LTDTLQAETDQLEDKKSALQTEIANLLKEKEK LEFILAAY The following letter code has been used:
A=alanine, C=cysteine, D=aspartic acid, E=glutamic acid, G=glycine, I=isoleucine, K=lysine, L=leucine, M=methionine, N=asparagine, Q=glutamine, R=arginine, S=serine, T=threonine, V=valine, Y=tyrosine According to the present state of knowledge, the leucine radicals therein, which are arranged at regular intervals of 7 amino acids (underlined in the formulae above), are active. The c-jun "leucine zipper peptide" (SEQ ID NO:1) shows, in contrast to the c-jun gene product, no homodimerization. The v-Fos "leucine zipper peptide" (SEQ ID NO:2) shows, similar to the intact v-fos gene product, no great tendency to homodimerization but—as already mentioned above—forms very stable heterodimeric complexes with the c-Jun "leucine zipper peptide" (SEQ ID No1) (E.K . O'SHEA et al., Science 245, 646–648 (1989) and M. NEUBERG et al., Nature 341 243–245 (1989)).

"Leucine zipper peptides" within the meaning of this invention are peptides which contain leucine residues arranged in the manner indicated above, and preferred peptides contain the c-Jun and v-Fos sequences. c-Jun and v-Fos are very particularly preferred.

Unexpectedly, the "leucine zipper peptides" proved when used according to the invention both as solid-phase reagents, trap reagents and as detection reagents to be superior to the conventional reagents of this type (protein A, protein G, polyclonal or monoclonal anti-bodies) because of their extremely high complex stability.

The invention relates to the use of pairs of peptides with extremely high specific affinity for one another in the area of in vitro diagnosis, these peptides being "leucine zipper peptides".

The invention furthermore relates to a heterogeneous immunochemical method for the determination of an analyte, where the specific binding partner bound to the solid phase is bound to the solid phase via a pair of "leucine zipper" peptides.

The invention also relates to a universal solid phase for use in heterogeneous immunochemical methods for the determination of an analyte, where one peptide of the pair of "leucine zipper" peptides is attached by adsorption or covalently, directly or via a spacer, to the solid phase.

The invention also relates to a universal reagent for use in immunochemical methods, where at least one peptide of the pair of "leucine zipper" peptides is bound to the specific binding partner serving for detection, and the second peptide of this pair is bound to a signal-emitting component.

The method according to the invention also makes it possible to bind more than one molecule of the second peptide of the pair of "leucine zipper" peptides to the specific binding partner serving for detection, either directly or via a carrier molecule or particle, and thus to obtain a signal increase which can be specifically adjusted.

The invention therefore also relates to a method for increasing the signal from the immunoassay, where more than one molecule of the second peptide of the pair of "leucine zipper" peptides is bound to the specific binding partner, directly or via a carrier molecule.

Since both the Fos and Jun "zipper peptide" and the corresponding intact gene products are readily soluble in water because of their hydrophilic nature, both peptides or gene products can be used for coupling to a solid phase. Suitable solid phases are known to the person skilled in the art. Typical examples of solid phases which can be used are, for example, tubes or shaped articles made of a plastic such as polystyrene or of a polyamide such as, for example, nylon, membrane-like structures or magnetizable particles, for example paramagnetic particles. Each peptide can moreover be attached by adsorption or covalently, directly or via a spacer, for example another peptide or protein or a smaller molecule, to the solid phase.

The corresponding complementary "zipper peptide" can be bound, for example, to an antibody or an antigen by methods known per se to the person skilled in the art. The antibodies can be mono- or polyclonal. Antigens within the meaning of the invention can also be haptens.

Other examples of the use according to the invention are covalent linkages of the above peptides with other ligands and enzymes, receptors, cytokines, lymphokines, catalytic antibodies, domain antibodies, complexons and other fusion proteins. The covalent linkages can take place both via sulfhydryl and amino groups and via carbohydrate residues by means of suitable linkers.

Since the amino-acid sequences of these "zipper peptides" are known, the question of the bioavailability is not a difficulty, given the current state of the art and the ease of obtaining amino acids. State of the art are automated peptide synthesizers which are able to provide within a short time defined, reproducible and, in particular, contamination-free peptides. This dispenses with, for example, the time-consuming isolation methods whose reproducibility depends not least on the quality of the material processed. Also essential to the invention is the inclusion of a required functionalization of the peptide in the synthesis step. In order, for example, to make possible subsequent covalent linkage of the Fos zipper peptide to any required carrier protein via a sulfhydryl group outside the leucine zipper sequence, for example a cysteine is synthesized on via two glycines to the amino terminus of the Fos leucine zipper peptide. It would be possible for other extension peptides which are likewise suitable to contain any desired number of amino acids and several cysteines. The cysteine SH group obtained in this way can then be used, for example, for derivatization and/or coupling to monoclonal antibodies.

This can be carried out, for example, in such a way that maleimido groups are introduced into an antibody in a manner known per se, for example by reaction with N-(gamma-maleimidobutyryloxy)succinimide, and the Fos leucine zipper peptide is added via the terminal cysteine SH group onto the maleimido double bond. In this case the coupling takes place via one of the amino groups of the MAb to the SH group of the cysteine in the Fos peptide.

It is alternatively possible also to link the Fos or Jun leucine zipper peptide to antibodies via the hinge region (disulfide bridges) of the antibody, for example by monofunctionalization with a bis-maleimide of the Fos leucine zipper peptide via the terminal cysteine SH group in a manner known per se, and then addition via the second maleimido group which has been introduced and is still unchanged onto to the hinge thiol groups of the antibody which has, for example, been reduced with dithiothreitol. This second method has the advantage that the linkage of the Fos or Jun leucine zipper peptide to the antibody takes place in a targeted manner outside the antigen binding site.

FIGS. 1 to 4 show diagrammatically the possibilities in principle of a wide-ranging and worthwhile use of the Jun-Fos interaction for in vitro diagnosis by way of example. An essential difference from the technologies already mentioned above is that the Jun/Fos interaction comprises a high-affinity system of two low molecular weight substances. The lower molecular weights result in a considerably greater degree of flexibility and thus in the achievement of tailored solutions. Binding of the peptides to biomolecules without loss of their biological activity is possible because of the modest spatial demands thereof. There is less severe limitation of methods limited by massive steric hindrances. Furthermore, the low molecular weights permit constructs which are easy to synthesize and which as "coupler components" not only are superior to, for example, the streptavidin stoichiometry of, in theory, four binding sites per molecule, but also can be freely designed. The direct consequence of this is a controllable increase in the sensitivity of diagnostic systems.

In this connection the following procedures are possible for providing the universal solid phases which can be achieved, for example, on polystyrene vessels, magnetic particles, latex particles etc.:

a) by adsorption using optimized coating methods b) covalently by chemical linkage to a functionalized solid phase c) by adsorption following previous covalent linkage of a zipper peptide to a carrier molecule which can be readily adsorbed d) covalently by linkage of a functionalized solid phase to a carrier molecule to which a zipper peptide is chemically bonded.

The specific solid phase is prepared using the peptide heterodimer formation in a secondary reaction with the complementary peptide conjugated with the specific binding partner.

Figure 1:
FIG. 1 shows a solid phase.
Figure 1:
Figure 1:
Figure 1:
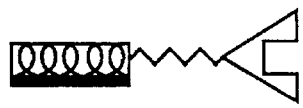
Figure 1:
Figure 1:
Figure 1:
Figure 1:
Figure 1:
Figure 2:
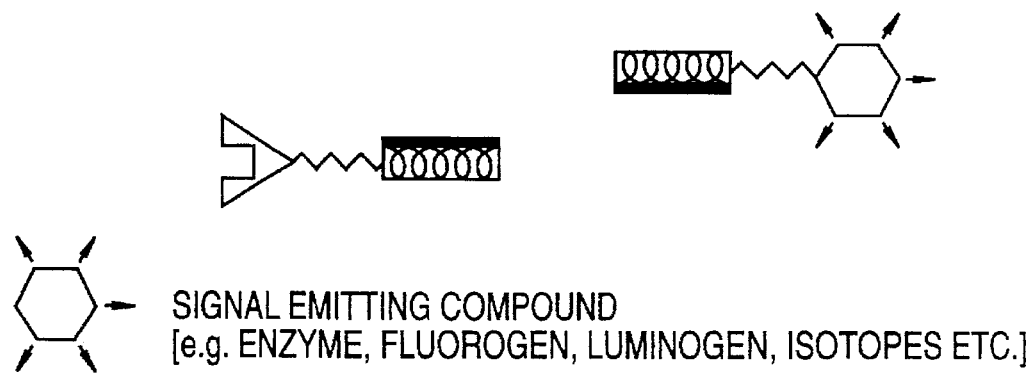

FIG. 2 shows a conjugate.

A zipper peptide is conjugated with the required incorporation rates with the specific binding partner by known coupling methods. Signal emission takes place after secondary reaction with a peptide which is complementary to the first and to which is linked any desired signal-emitting component (for example enzyme, fluorogen, luminogen, radionuclide etc.).

Figure 3A:
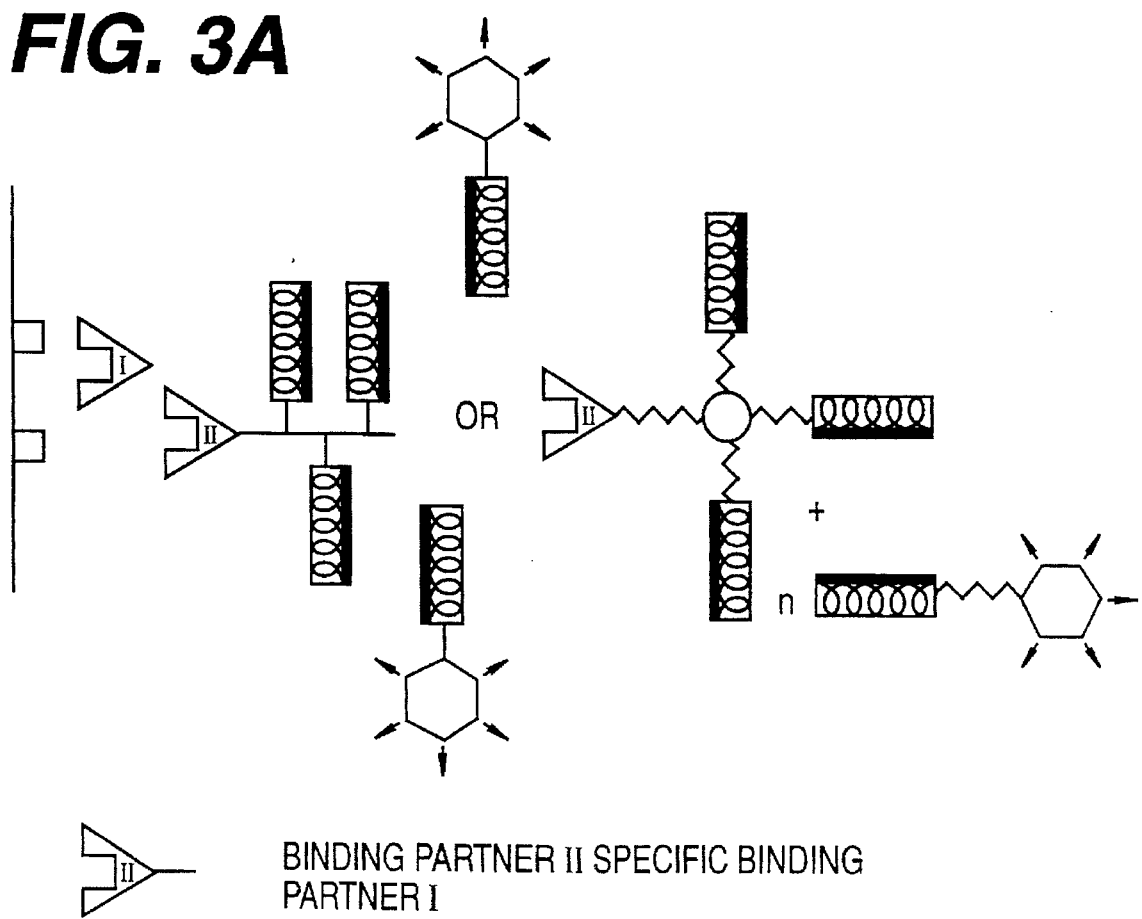

FIGS. 3a)–3c) show an amplification system.

The amplification of any desired signal can be achieved using the zipper peptides in the following manner:

a) A second specific binding partner which is directed against a first specific binding partner which recognizes the antigen is either substituted several times with a zipper peptide or, for steric reasons, linked to a peptide-carrying carrier molecule.

b) The specific binding partner is substituted with the same peptide as the signal-emitting component. The "coupling" of these two components is achieved using a carrier molecule to which the peptide which is complementary to the first is coupled in the required incorporation rate.

c) Amplification is brought about by using a preformed complex between the "coupler component" described under b) and the signal-emitting component provided with peptide.

Figure 4:
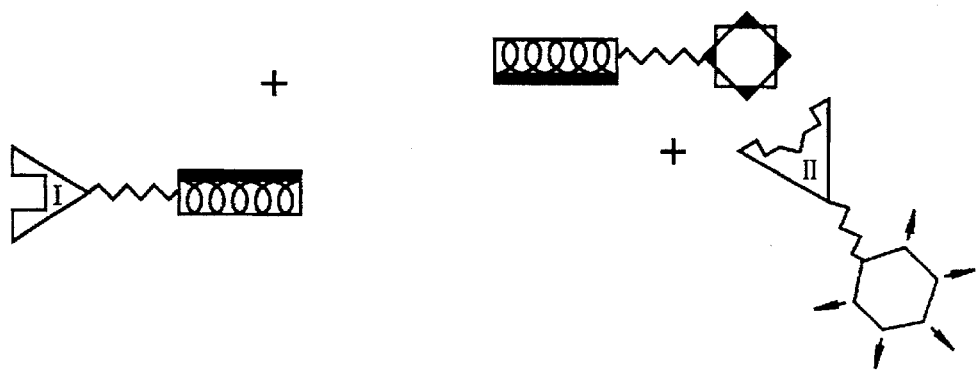
Figure 4:
Figure 4:
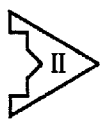

FIG. 4 shows artificial control serum/standards.

A first specific binding partner which is linked to a zipper peptide recognizes the antigen. There is formation in a secondary reaction of the heterodimer with a peptide which is complementary to the first and which is conjugated with any desired antigenic structure (for example peptide, protein etc.) and is directed against the second specific binding partner which is linked to a signal-emitting component.

The following examples serve to illustrate the invention and in no way restrict it.

EXAMPLE 1

Step 1:
Coating of microtiter plates with Jun peptides

150 µl of a solution containing 10 µg/ml Jun peptide in 0.1M sodium carbonate are placed in each of 16 wells of microtiter plates supplied by Nunc, Roskilde, Denmark. The assay plates charged with the dilutions are left at 20° C. for 18 hours, then the solutions in the wells are removed by aspiration and the wells are washed 3–4 times with 300 µl of a solution of 10 g/l of bovine serum albumin in phosphate-buffered physiological saline (PBS, pH 7.4) by filling and removal by aspiration, and the assay plates are then dried at 20° C. over silica gel.

Step 2:
Preparation of a maleimido-antibody

The antibody to be conjugated (concentration 4 mg/ml in PBS; 2.5 ml) is mixed with lithiumborate buffer (2.5 ml) (see below for preparation). To the resulting solution with a pH of 7.5 are added, while stirring, 0.45 ml of a 13 mg/ml solution of GMBS (N-gamma-maleimidobutyryloxy-succinimide) in dioxane (corresponding to a 30-fold molar excess of GMBS over IgG). After incubation at room temperature for one hour, the excess reagent is removed by gel filtration on a Sephadex G-25 column equilibrated with phosphate-buffered saline (PBS), pH 7.2.

Preparation of the lithium borate buffer, pH 8.5:

1.24 g of boric acid are stirred into a mixture of water (80 ml) and dioxane (20 ml). Solid lithium hydroxide is added while dissolving the boric acid to adjust to a pH of 8.5.

Step 3:
Coupling of the Fos leucine zipper peptide to a maleimido-antibody.

The maleimido-antibody (2 mg in 2 ml of PBS) prepared as in Step 2 is incubated with 1 equiv. of Fos leucine zipper peptide (64 µg in 100 µl of PBS) at room temperature for 1 h. This is followed by gel filtration through an AcA 34 column (diameter 2.5 cm; height 45 cm) with a sodium chloride/sodium citrate buffer, pH 7.3 (0.4M sodium chloride and 0.04M sodium citrate).

Step 4:
Preparation of a peroxidase-labeledantibody and of a TMB substrate for detection Antibodies are generated by the method of KOEHLER and MILSTEIN for preparing monoclonal antibodies (Nature 256, 495, 1975), and different monoclonal antibodies with the same antigen specificity have been identified by the method described by STAHLI et al. (J. of Immunological Methods 32, 297–304, 1980). After purification by gel chromatography, and dialysis against phosphate-buffered saline (PBS, pH 7.4), the pool containing the monoclonal antibody fraction (4 mg of protein/ml) is subsequently reacted with N-gamma-maleimidobutyryloxysuccinimide (GMBS) obtained from Calbiochem, as described by TAN-AMORI et al. (J. Immunol. Meth. 62, 123–131, 1983).

Final dilutions of the solutions of the antibody-POD conjugates obtained in this way are made for each assay use. Used as conjugate dilution medium is a buffer containing 0.1M 2-amino-2-(hydroxymethyl)-1,3-propanediol (TRIS), 0.5% $^R$Tween 20, 0.5–1% stabilizing protein pH 7.4. Polyclonal antibodies prepared according to the state of the art are adjusted in the same way.

A substrate system or a substrate preparation containing hydrogen peroxide and tetramethylbenzidine (TMB), which is prepared from two stock solutions, is used to detect Ab-IgG/POD conjugate.

Stock solution 1: TMB dihydrochloride is dissolved at a concentration of 5 g/l, i.e. of 16 mmol/l, by stirring in double-distilled water and adjusted to pH 1.5 with 5 normal hydrochloric acid. Penicillin G is added at a final concentration of 200 mg/l, i.e. of 0.56 mmol/l, to this solution while stirring.

Stock solution 2: 1.4 ml of glacial acetic acid, 1.5 ml of 1 normal NaOH and 250 mg, i.e. 3 mmol, of $H_2O_2$ in the form of urea-hydrogen peroxide adduct are added to 900 ml of double-distilled water. After dissolution is complete, the volume is made up to 1 l with double-distilled water.

TMB substrate preparation: one part by volume of stock solution 1 and 10 parts by volume of stock solution 2 are mixed together.

Step 5

Determination of antigen in an ELISA using the peptides according to the invention 10 μl of a solution containing 0.01 mg/ml of the Fos peptide-antibody conjugate prepared as in Step 3, in sodium chloride/sodium citrate buffer, are placed in the wells of microtiter plates which are coated with peptides as described. It is possible where appropriate to remove the solution by aspiration after 10–30 min and to wash the wells. 20 μl of serum or plasma, 10 μl of incubation medium (BW, OSND) are placed in the wells. After incubation at 37° C. for 30 min, the contents of the wells are removed by aspiration and the wells are washed three times with washing buffer containing 1 g/l $^R$Tween 20 in PBS. This is followed by addition of 100 μl of conjugate in the final dilution to the wells. After incubation at 37° C. for 30 min, the contents of the wells are removed by aspiration, and again three washes are carried out. Subsequently 100 μl of TMB substrate preparation are added to each well, incubated at 20°–22° C. for 30 min, and incubation is stopped by adding 100 μl of 1 normal sulfuric acid. The extinction of the colored solution is measured at a wavelength of 450 nm ($E_{450}$) with PBS as reference.

EXAMPLE 2

Step 1

Coating of microtiter plates

150 μl of a solution containing 5 μg/ml Jun or Fos peptide in 50 mM carbonate buffer are placed in each of the wells of microtiter plates supplied by Nunc, Roskilde (Denmark). The charged assay plates are left at room temperatures overnight, then the solutions in the well are removed by aspiration, and the wells are washed three times with 250 μl of a phosphate-buffered physiological saline by filling and aspirating out. The assay plates are then left to dry over silica gel at 20° C.

Step 2

Preparation of a maleimido-antibody

The antibody to be conjugated (concentration 4 mg/ml in PBS; 1 ml) is mixed with lithiumborate buffer (1 ml). To the resulting solution with a pH of 8.0 are added, while stirring, 0.017 ml of a 13 mg/ml solution of GMBS (N-gamma-maleimmidobutyryloxy-succinimide) in dioxane (corresponding to a 30-fold molar excess of GMBS over IgG). After incubation at room temperature for one hour, the excess reagent is removed by gel filtration on a Sephadex G-25 column equilibrated with phosphate-buffer pH 6.0 containing 5 μM Titriplex I.

Step 3

Coupling of the Jun or Fos leucine zipper peptide to a maleimido-antibody

The maleimido-antibody prepared as in Step 2 (2 mg in 2 ml of phosphate buffer pH 6.0 containing 5 μM Titriplex I) is incubated with one equivalent of Jun or Fos leucine zipper peptide (15 mg in 1 ml of PBS) at room temperature for 1 hour. This is followed by gel filtration through a Sephadex G-25 column (diameter 1 cm; height 15 cm) with 50 mM tris pH 7.4.

Step 3 a)

Coupling of a functionalized Jun or Fos leucine zipper peptide to a maleimido-antibody 2.1 mg of Jun or Fos peptide are taken up in 0.21 ml of PBS and mixed with 9.5 μl of a SAMSA stock solution (S-acetylmercaptosuccinic anhydride; FLUKA; 22.2 mg/ml in dioxane). After reaction at room temperatures for 30 minutes, the solution is treated with 60 μl of a 1M $NH_2OH$ solution in water and incubated at room temperature for a further 15 minutes. The reaction mixture is then desalted on a Biogel P2 column with phosphate buffer pH 6 containing 5 μM Titriplex I.

The subsequent coupling procedure to a maleimido-antibody is carried out in analogy to Step 3.

Step 4

Determination of CEA in an ELISA using the peptides according to the invention

100 μl of a 0.01 mg/ml Fos peptide-anti-CEA antibody conjugate prepared as in Step 2 in buffer (OSND, Behringwerke) are placed in the wells of microtiter plates which have been coated with Jun peptide as described. It is possible where appropriate for the solution to be removed by aspiration after 2 hours at 37° C. and for the wells to be washed with Enzygnost washing buffer (OSEW). 20 μl of serum or CEA standard and 100 μl of the anti-CEA antibody in final dilution (for example polyclonal, rabbit), which is in peroxidase-labeled form, are placed in the wells. After a reaction time of 2 hours at 37° C., the contents of the wells are removed by aspiration and washing with washing buffer is again carried out. Finally, 100 μl of TMB substrate preparation are placed in each well, incubated at room temperature for 30 minutes, and the incubation is stopped by adding 100 μl of 1 normal sulfuric acid. The extinction of the colored solution is measured at a wavelength of 450 nm with PBS as reference.

Exemplary embodiment A: standard plot of the CEA-ELISA with the peptides according to the invention

TABLE 1

| CEA concentration (ng/ml) | 0 | 1 | 3 | 10 | 30 | 100 |
|---|---|---|---|---|---|---|
| Extinction | | | | | | |
| 450 nm (mE) | 14 | 40 | 93 | 321 | 980 | 2471 |
| | 17 | 37 | 103 | 346 | 1067 | 2408 |
| Mean extinction (mE) | 16 | 40 | 98 | 334 | 1024 | 2440 |

Exemplary embodiment B:

Correlation of the CEA ELISA with the peptides according to the invention compared with other commercial CEA assays The CEA determines were carried out with an ELISA with the peptides according to the invention in analogy to Exemplary embodiment A, but this time in an inverse system with a Fos peptide-coated microtiter plate and a Jun-anti-CEA conjugate.

TABLE 2

Agreement of the CEA concentrations on comparison with a commercial assay

| | CEA concentrations (ng/ml) in normal sera | | | | | |
|---|---|---|---|---|---|---|
| Enzygnost CEA micro (Behringwerke AG) | 1.49 | 1.32 | 1.05 | 1.05 | 1.26 | <1.0 |
| "Jun/Fos"-CEA ELISA | 1.22 | 1.94 | 1.5 | 1.88 | 1.74 | 1.3 |

| | CEA concentrations (ng/ml) in tumor sera | | | | | |
|---|---|---|---|---|---|---|
| Enzygnost CEA micro (Behringwerke AG) | 3.6 | 6.9 | 7.2 | 17.6 | 9.8 | 28.6 |
| "Jun/Fos"-CEA ELISA | 3.53 | 9.3 | 9.8 | 20.7 | 10.1 | 27.8 |
| Enzygnost CEA micro (Behringwerke AG) | 39.9 | 29.3 | 87.2 | 105.5 | 1538 | 5180 |
| "Jun/Fos"-CEA ELISA | 36.2 | 36.2 | 121.6 | 106.9 | 1276 | 5201 |

Result:

Direct comparison with a commercial CEA assay kit revealed very good correlation of the CEA concentrations (correlation coefficient r=0.999).

Step 5

Determination of AFP in an ELISA using the peptides according to the invention

100 μl portions of a Jun peptide-anti-AFP antibody conjugate (anti-AFP antibodies from sheep) prepared as in Example 2, Step 3 or 3a are pipetted into the wells of microtiter plates which were coated with Fos peptide as in Example 2, Step 1, and incubated at 37° C. for 2h. After the wells had been washed three times with washing buffer (OSEW, Behringwerke), 20 μl portions of standard or sample and 100 μl of a buffer (OSND, Behringwerke) with the addition of peroxidase-conjugated anti-AFP antibodies from sheep were introduced. The two-hour incubation at 37° C. is again stopped with a washing step (see above), and the substrate/chromogen reaction is carried out as in Example 2, Step 4.

The Jun peptide-anti-AFP antibodies are employed in a concentration range from 25 to 0.5 μg/ml appropriate for the chosen concentration of the peroxidase-conjugated anti-AFP antibodies so that the measured signal at 450 nm for the standard S5 (300 IU/ml) amounts to a minimum extinction of 0.8 E.

Exemplary embodiments of the Jun/Fos AFP assay:

A) Specificity of the Jun-Fos interaction I

In order to check the specificity of the Jun-Fos interaction, various peptide-coated and uncoated microtiter plates were employed in analogy to the assay procedure described above in combination with anti-AFP antibodies to which Jun or Fos peptide or no peptide have been coupled.
Result:

Only when the "Fos solid phase" was used in combination with Jun-anti-AFP antibodies was it possible to obtain with the standard S5 (300 IU AFP/ml) a measured signal which was significantly higher than with the standard S0 (0 IU AFP/ml) (Tab. 3).

TABLE 3

Specificity of the Jun-Fos interaction

| | Measured signal (extinction) | |
|---|---|---|
| | Standard S0 (0 IU AFP/ml) | Standard S5 (300 IU AFP/ml) |
| a) Microtiter plate uncoated: | | |
| Jun-anti-AFP antibody: | 0.007 | 0.026 |
| Fos-anti-AFP antibody: | 0.011 | 0.017 |
| anti-AFP antibody: | 0.009 | 0.017 |
| b) Jun-coated microtiter plate: | | |
| Jun-anti-AFP antibody: | 0.008 | 0.061 |
| c) Fos-coated microtiter plate: | | |
| Jun-anti-AFP antibody: | 0.006 | 3.250 |
| Fos-anti-AFP antibody: | 0.009 | 0.012 |
| anti-AFP antibody: | 0.009 | 0.017 |
| no anti-AFP antibody: | 0.010 | 0.011 |

B) Specificity of the Jun-Fos interaction II

The Jun/Fos AFP assay described hereinbefore was preceded by an incubation step with 100 μl in each case of a Jun or Fos peptide-containing buffer solution (buffer=OSND) per well at 37° C. for one hour. After 3 washes, the subsequent assay procedure was as specified above.
Result:

Only by addition of free Jun peptide was it possible to inhibit the binding of Jun-anti-AFP antibody to the Fos-coated solid phase (Tab. 4)

TABLE 4

Inhibition of the Jun-anti-AFP antibody binding to the Fos-coated microtiter plate by addition of free peptide

| | | Measured signal (extinction 450 nm) | |
|---|---|---|---|
| | Free peptide (μg/ml) | Standard S0 (0 IU AFP/ml) | Standard S5 (300 IU AFP/ml) |
| Jun | 0 | 0.010 | 3.590 |
| | 5 | 0.015 | 3.486 |
| | 50 | 0.011 | 2.857 |
| | 500 | 0.013 | 1.371 |
| Fos | 0 | 0.007 | 3.599 |
| | 5 | 0.010 | 3.416 |
| | 50 | 0.011 | 3.572 |
| | 500 | 0.015 | 3.694 |

C) Standard plot for Jun/Fos AFP assay:

TABLE 5

| Standard plot for the Jun/Fos AFP assay | | | | | | |
|---|---|---|---|---|---|---|
| AFP concentration (IU/ml) | 0 | 3 | 10 | 30 | 100 | 300 |
| Extinction 450 nm | 0.009 | 0.021 | 0.101 | 0.396 | 0.631 | 0.883 |
|  | 0.009 | 0.024 | 0.071 | 0.296 | 0.699 | 0.916 |
| Mean extinction | 0.009 | 0.023 | 0.086 | 0.346 | 0.665 | 0.900 |

We claim:

1. A method for in vitro immunochemical detection and determination of an analyte in a biological liquid using a pair of complementary leucine zipper peptides, wherein the first leucine zipper peptide of the pair of leucine zipper peptides specifically binds to the second leucine zipper peptide of the pair of leucine zipper peptides, comprising the steps of:

(a) immobilizing said first leucine zipper peptide on a solid phase;

(b) coupling said second leucine zipper peptide to a specific binding partner for the analyte;

(c) contacting the immobilized first leucine zipper peptide with the second leucine zipper peptide coupled to the specific binding partner for the analyte, thereby immobilizing the specific binding partner on the solid phase;

(d) contacting a sample of the biological liquid containing the analyte with the immobilized specific binding partner; and (e) determining the amount of the analyte bound by said specific binding partner.

2. The method of claim 1, wherein the specific binding partner is an antibody.

3. The method of claim 1, wherein the first leucine zipper peptide is one of v-Fos and c-Jun and the second leucine zipper peptide is the other.

4. A method for in vitro immunochemical detection and determination of an analyte in a biological liquid using a pair of complementary leucine zipper peptides, wherein the first leucine zipper peptide of the pair of leucine zipper peptides specifically binds to the second leucine zipper peptide of the pair leucine zipper peptides, comprising the steps of:

(a) coupling said first leucine zipper peptide to a signal-emitting component;

(b) coupling said second leucine zipper peptide to a first specific binding partner for the analyte;

(c) contacting the first leucine zipper peptide coupled to the signal-emimitting component with the second leucine zipper peptide coupled to the specific binding partner for the analyte to form a complex;

(d) coupling a second specific binding partner for the analyte to a solid phase;

(e) contacting a sample of the biological liquid containing the analyte with said complex and with said second specific binding partner coupled to the solid phase; and (f) determining the amount of analyte being bound by the second specific binding partner.

5. The method of claim 4, wherein the first and second specific binding partners are each an antibody.

6. The method of claim 4, wherein the first leucine zipper peptide is one of v-Fos and c-Jun and the second leucine zipper peptide is the other.

7. A solid phase reagent for in vitro immunochemical detection and determination of an analyte in a biological liquid, consisting essentially of:

a solid phase; and a pair of complementary leucine zipper peptides consisting of a first leucine zipper peptide and a second leucine zipper peptide, wherein the first leucine zipper peptide of the pair of leucine zipper peptides specifically binds to the second leucine zipper peptide of the pair of leucine zipper peptides;

wherein the first leucine zipper peptide is immobilized on said solid phase, the second leucine zipper peptide is coupled to a specific binding partner for the analyte, and the second leucine zipper peptide is complexed with the first leucine zipper peptide.

8. A universal reagent for in vitro immunochemical detection arid determination of an analyte in a biological liquid, consisting essentially of a pair of complementary leucine zipper peptides consisting of a first leucine zipper peptide and a second leucine zipper peptide, wherein the first leucine zipper peptide of the pair of leucine zipper peptides specifically binds to the second leucine zipper peptide of the pair of leucine zipper peptides, wherein the first leucine zipper peptide is coupled to signal-emitting component and the second leucine zipper peptide is coupled to a specific binding partner for the analyte.

9. In a method of in vitro immunochemical detection or determination of an analyte in a biological liquid comprising attaching a specific binding partner of an analyte to a solid phase via a specific binding pair which does not react with the analyte, contacting a sample of biological liquid containing the analyte with the immobilized specific binding partner, and determining the amount of analyte being bound to the specific binding partner, wherein the improvement comprises:

(a) immobilizing a first leucine zipper peptide of a pair of complementary leucine zipper peptides to a solid phase, wherein the first leucine zipper peptide of the pair of leucine zipper peptides specifically binds to a second leucine zipper peptide of the pair of leucine zipper peptides;

(b) coupling said second leucine zipper peptide to a specific binding partner for the analyte; and (c) contacting the first leucine zipper peptide with the second leucine zipper peptide to immobilize said specific binding Gartner for the analyte to the solid phase.

10. In a method of in vitro immunochemical detection or determination of an analyte in a biological liquid comprising attaching a first specific binding partner of an analyte to a solid phase via a specific binding pair which does not react with the analyte, contacting a sample of biological liquid with the immobilized specific binding partner, and determining the amount of analyte being bound to the specific binding partner through the use of a labeled second specific binding partner for the analyte, wherein the improvement comprises:

(a) coupling a first leucine zipper peptide of a pair of complementary leucine zipper peptides to a signal-emitting component, wherein the first leucine zipper peptide of the pair of leucine zipper peptides specifically binds to a second leucine zipper peptide of the pair of leucine zipper peptides;

(b) coupling said second leucine zipper peptide to the second specific binding partner for the analyte; and (c) contacting the first leucine zipper peptide with the second leucine zipper peptide, thereby attaching the signal-emitting component to the second specific binding partner for the analyte.

11. A method of amplifying the signal in an immunoassay for an analyte, comprising the steps of:

(a) coupling first leucine zipper peptides of a pair of leucine zipper peptides to a signal-emitting component, wherein the first leucine zipper peptides of the pair of leucine zipper peptides specifically binds to a second leucine zipper peptides;

(b) coupling more than one molecule of the second leucine zipper peptide to a second specific binding partner which specifically binds to a first specific binding partner which specifically binds to the analyte;

(c) contacting the first leucine zipper peptides coupled to the signal-emitting components with the second leucine zipper peptides coupled to the specific binding partner to form a complex;

(d) contacting a sample of biological fluid containing the analyte with the complex; and (e) determining the amount of analyte bound by the first specific binding partner.

12. The method claim 11, wherein the first specific binding partner is an antibody.

13. The method of claim 11, wherein the first leucine zipper peptide is one of v-Fos and c-Jun and the second leucine zipper peptide is the other.

14. The method of claim 11, wherein the second specific binding partner is coupled to the more than one molecules of the second leucine zipper peptide via a carrier molecule.

\* \* \* \* \*

UNITED STATES PATENT AND TRADEMARK OFFICE
CERTIFICATE OF CORRECTION

PATENT NO. : 5,643,731
DATED : July 01, 1997
INVENTOR(S) : Klaus Bosslet et al.

It is certified that error appears in the above-identified patent and that said Letters Patent is hereby corrected as shown below:

Claim 4, column 12, line 62, after "pair", insert --of--.

Claim 4, column 13, line 2, "signal-emimitting " should read --signal-emitting--.

Claim 8, column 13, line 34, "arid" should read --and--.

Claim 12, column 14, line 49, after "method", insert --of--.

Signed and Sealed this

Twenty-first Day of July, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 40 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
                20                  25                  30

Leu Lys Gln Lys Val Met Asn Tyr
                35              40

( 2 ) INFORMATION FOR SEQ ID NO:2:

( i ) SEQUENCE CHARACTERISTICS:
( A ) LENGTH: 40 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Leu Thr Asp Thr Leu Gln Ala Glu Thr Asp Gln Leu Glu Asp Lys Lys
1               5                   10                  15

Ser Ala Leu Gln Thr Glu Ile Ala Asn Leu Leu Lys Glu Lys Glu Lys
                20                  25                  30

Leu Glu Phe Ile Leu Ala Ala Tyr
                35              40